United States Patent
Kankkunen et al.

[19]

[11] Patent Number: 5,819,814
[45] Date of Patent: Oct. 13, 1998

[54] METHOD AND ASSEMBLY FOR FILLING AN ANESTHETIC EVAPORATOR

[75] Inventors: Jukka Kankkunen, Vantaa; Erkki Heinonen, Helsinki, both of Finland

[73] Assignee: Instrumentarium Oy, Helsinki, Finland

[21] Appl. No.: 773,432

[22] Filed: Dec. 27, 1996

[30] Foreign Application Priority Data

Dec. 28, 1995 [FI] Finland .................................. 956305

[51] Int. Cl.⁶ ...................................................... B65B 1/04
[52] U.S. Cl. .................................. 141/18; 141/59; 141/2; 141/311 A
[58] Field of Search .................................. 141/2, 18, 21, 141/45, 59, 61, 198, 285, 286, 289, 290, 291, 292, 293, 295, 308, 309, 346–352, 363–366, 311 A, 319–321, 353–355, 357, 382, 115–120; 128/200.19, 200.16, 200.21; 137/207.5

[56] References Cited

U.S. PATENT DOCUMENTS 3,565,133  2/1971  Jones ........................................ 141/308
4,883,049  11/1989  McDonald .

FOREIGN PATENT DOCUMENTS 448954   10/1991  European Pat. Off. .
455433   11/1991  European Pat. Off. .
923196   12/1994  Finland .
944888   3/1996   Finland .
4106756  9/1992   Germany .
2177008  1/1987   United Kingdom .
95/15778 6/1995   WIPO .

*Primary Examiner*—J. Casimer Jacyna
*Assistant Examiner*—Steven O. Douglas
*Attorney, Agent, or Firm*—Andrus, Sceales, Starke & Sawall

[57] ABSTRACT

A method and an assembly for filling an anesthetic evaporator, comprises a filling device (1) connectable to a transport container (15) and having a filling head (2) which can be inserted in an attachment point (4) included in an evaporator (3), the filling device and evaporator being provided with conduits (5a, 5b, 6a, 6b) for passing an anesthetic and a substituting gas between the transport container and the evaporator and the assembly comprising a clamping implement (7) for tightening the filling head (2) against a packing surface of the conduits arriving in the attachment point (4) included in the evaporator and a valve element (8, 9), adapted to open and thus to allow a flow of the anesthetic and the substituting gas. In view of eliminating leaks, the conduits (5a, 6a) included in the filling device (1) and intended for the transfer of an anesthetic and the transfer of a substituting gas are adapted to be in communication with each other whenever the conduits between the filling container (15) and the evaporator liquid tank (16) are closed.

18 Claims, 3 Drawing Sheets

METHOD AND ASSEMBLY FOR FILLING AN ANESTHETIC EVAPORATOR

BACKGROUND OF THE INVENTION

Field of the Invention

The present invention relates to a method for filling an anesthetic evaporator, wherein the filling head of a filling device connectable to an anesthetic transport container is inserted in an attachment point included in the evaporator for passing the anesthetic between the transport container and the evaporator and for passing a substituting gas in the opposite direction along conduits included in the filling device and the evaporator, and in which method the filling head is tightened by means of a clamping implement against a packing surface of the conduits arriving in the attachment point included in the evaporator, one or more valve elements opening and thus allowing a flow of the anesthetic between the evaporator and the transport container and a flow of the substituting gas in the direction opposite to that of the anesthetic between the transport container and the evaporator. The invention relates also to an assembly for filling an anesthetic evaporator.

The anesthetics used in the anesthetization of a patient and administered by way of a respiratory gas are called inhalation anesthetics. These include for example halotane, enflurane and isoflurane.

The anesthetics are delivered to the site of administration in a liquid state. A gaseous state for the administration thereof is achieved in an anesthetic evaporator, which is a device specific to each anesthetic. The liquid is passed from a transport container to the evaporator by means of a special filling device. Such filling devices make sure, by way of the design thereof, that a given type of evaporator can only be fitted with a transport container of the pertinent liquid or fluid.

In the prior art solutions, a filling device is attached to a bottle serving as a transport container, e.g. by screw-threading. In solutions like this, a filling head to be attached to the evaporator is a cubical element, having one side thereof provided with two flow ports, one for the flow of a liquid and the other for the flow of a substituting gas. Said filling head is inserted in a socket included in the evaporator therefor. The socket is provided with flow ports, which are in line with those of the filling head and extend by way of filling valves to a liquid tank included in the evaporator. The filling head is tightened in its socket in such a manner that a packing included in the junction of said flow ports seals the flow conduits.

When the filling head has been fitted to the flow port and the filling valves have been opened, the liquid tank of an evaporator and the bottle serving as a transport container produce, with the assistance of a filling device, a closed volume, wherein the liquid flows along one of the flow conduits of the filling device towards the tank located at a lower level. In the other conduit travels a gas flow, which substitutes for the liquid flow, towards the upper level tank. The evaporator and the transport container are rigid structures and, thus, the flow of a substituting gas is a must. Filling of the evaporator is performed by lifting the transport container above the liquid tank of the evaporator and evacuation of the evaporator, respectively, e.g. by lowering the transport container below the liquid tank of the evaporator.

In terms of filling, for example, it is essential that the filling head is tightened into the evaporator socket whenever the filling valves are open. If this is not the case, a liquid in the evaporator flows out through the filling valves and open flow ports and causes pollution of ambient air. In traditional evaporators, the tightening of a filling device in a socket included in the evaporator is effected by means of a special clamping screw. After the tightening, the opening of filling valves is effected by means of a separate actuator. When filling or evacuating an evaporator, the filling device must first be separately tightened in position, followed by separately opening the valves. When the filling is completed, it is necessary to first shut off the valves and, only as a final procedure, to disengage the filling device. As an applied connection, the procedure is complicated and offers a number of possibilities for malfunctions.

Attempts have been made to improve the traditional filling device by designing various types of mechanisms, which preclude opening of the filling valve unless the filling device is secured in position and, conversely, disengagement of the filling device unless the filling valve is shut off. One such solution is described in EP publication 455,433 A1. In this cited solution, the tightening of a filling device is effected with the assistance of friction. Being cubical in shape and smooth in its surfaces, however, the filling device may slip out of the socket whereafter, if the filling valves are open, the liquid will be able to flow out of the tank. Another drawback is a complicated mechanical construction.

In order to eliminate the drawbacks of a device as described above, a device has been developed in which the shutting-off of a filling valve occurs automatically upon removing the filling device from the socket. This solution is described in FI Patent application 923196. The solution has also been useful in simplifying the mechanical design by eliminating the need of tightening the filling device and of having a mechanical coupling between the filling valves. A drawback is the necessity to include an element identifying the immobilized position of a filling device and the load of a spring used in its mechanical implementation, which applies to the filling device and opposes the installation thereof.

Furthermore, in the above-described solutions, there is one essential drawback in the applied connection that has not been eliminated, namely that the tightening of a filling device and the opening of filling valves are effected by means of separate actuators.

The published DE-application 4,106,756 describes a solution in which, on the one hand, the open state of a filling valve always requires the immobilized position of a filling device and, on the other, the applied connection only includes a single actuator. In this apparatus, the filling valves are included in a clamping surface of the filling device in such a manner that the valves open automatically under compression from the filling device upon tightening or clamping the filling device in its position. The compression is effected by means of special, sliding, spring-loaded intermediate bushings. The end of these bushings facing the filling device is provided with a packing, used for sealing a junction between the filling device and the evaporator. The packing occurs at the early stage of tightening.

After the packing, as tightening is continued further, the pins included in the bushings press against spring-loaded balls serving as valves to open the same. Accordingly, as the filling is concluded, the unclamping of a filling device causes first the closure of the valves as a result of the force of said springs and, only after this has happened, the release of a packing surface between the evaporator and the filling device. Mechanically, the solution is ostensibly simple and easy in terms of its functionality, since the entire operation occurs by means of a single actuator.

However, a drawback in the above solution is the flow conduits, which become very cramped. The positioning and dimensioning of ports included in a filling device are standardized. The distance between the centres of ports is 6.25 mm. The flow ports of an evaporator have diameters of 3.2 and 4.8 mm. Thus, between the ports remains a space which is 2.25 mm. The construction of release bushings and packings therefor in this space is a job that requires extremely fine machining. On the other hand, reducing the size of flow ports to smaller than what is standardized constricts the flows and, thus, increases the filling time. This impairs remarkably the applicability of an evaporator filling mechanism.

Problems noted in the above-described filling systems included a confusing and hard-to-use applied connection, mechanical complexity, and a slow filling rate.

In view of eliminating the above problems, there has been developed an assembly as set forth in FI Patent application 944888, which has made it possible to resolve said problems in a preferred fashion.

However, the above solutions involve one drawback, which has escaped elimination. The problem relates to the operation of a filling valve and it can be described as follows. The traditional filling valve comprises a shut-off valve included both in a gas and in a liquid conduit and an actuator controlling those valves. The valves open and close under the action of the actuator either simultaneously or sequentially for achieving desired flow characteristics. As noted above, the filling is performed, after the filling device has been attached to both a transport container and an evaporator, by lifting the transport container above the evaporator. As the filling is concluded, it is essential, in order to preclude a liquid flow out of the evaporator, that the filling valves be closed before releasing the sealing between the filling head and the evaporator. The closure of filling valves results in the cut-off of both flow conduits between the transport container and the liquid tank of an evaporator. Thus, a conduit section between the filling valve and the transport container remains full of liquid. Upon lowering the transport container, the liquid tends to flow towards the transport container. Since the filling valves are closed and the filling head secured to the evaporator, a vacuum produced in the filling valve precludes the flow of liquid. A consequence of this is that, as the filling device is disengaged from the evaporator, the liquid trapped between the sealing and the filling valve escapes into the environment.

Upon vapourization, the liquid has a strong odour and can even be a health hazard after a long-term exposure. Therefore, efforts have been made to minimize the amount of escaping liquid. A generally applied approach is to locate the filling valves as close to the packing surface as possible. However, this does not eliminate the entire problem, as there always remains a space therebetween.

SUMMARY OF THE INVENTION

An object of the invention is to provide an assembly which is capable of eliminating the above drawback. This has been accomplished by means of the invention. A method of the invention is characterized in that the conduits included in the filling device and intended for the transfer of an anesthetic and for the transfer of a substituting gas, respectively, are fitted in communication with each other whenever the conduits between the transport container and the liquid tank of an evaporator are closed. On the other hand, an assembly of the invention is characterized in that the conduits included in the filling device and intended for the transfer of an anesthetic and for the transfer of a substituting gas, respectively, are adapted to be in communication with each other whenever the conduits between the transport container and the liquid tank of an evaporator are closed.

A benefit of the invention is first of all its simplicity, whereby the adoption and operating costs of the invention become attractive. By virtue of simplicity, the inventive assembly has a high reliability in operation. Another benefit of the invention is its flexibility, i.e. the invention can be applied to all existing equipment in which the evaporator is filled by coupling therewith a container carrying an anesthetic liquid.

BRIEF DESCRIPTION OF THE DRAWING

The invention will now be described in more detail with reference to one preferred exemplary embodiment depicted in the accompanying drawing, wherein.

DESCRIPTION OF THE PREFERRED EMBODIMENTS

Figure 1:
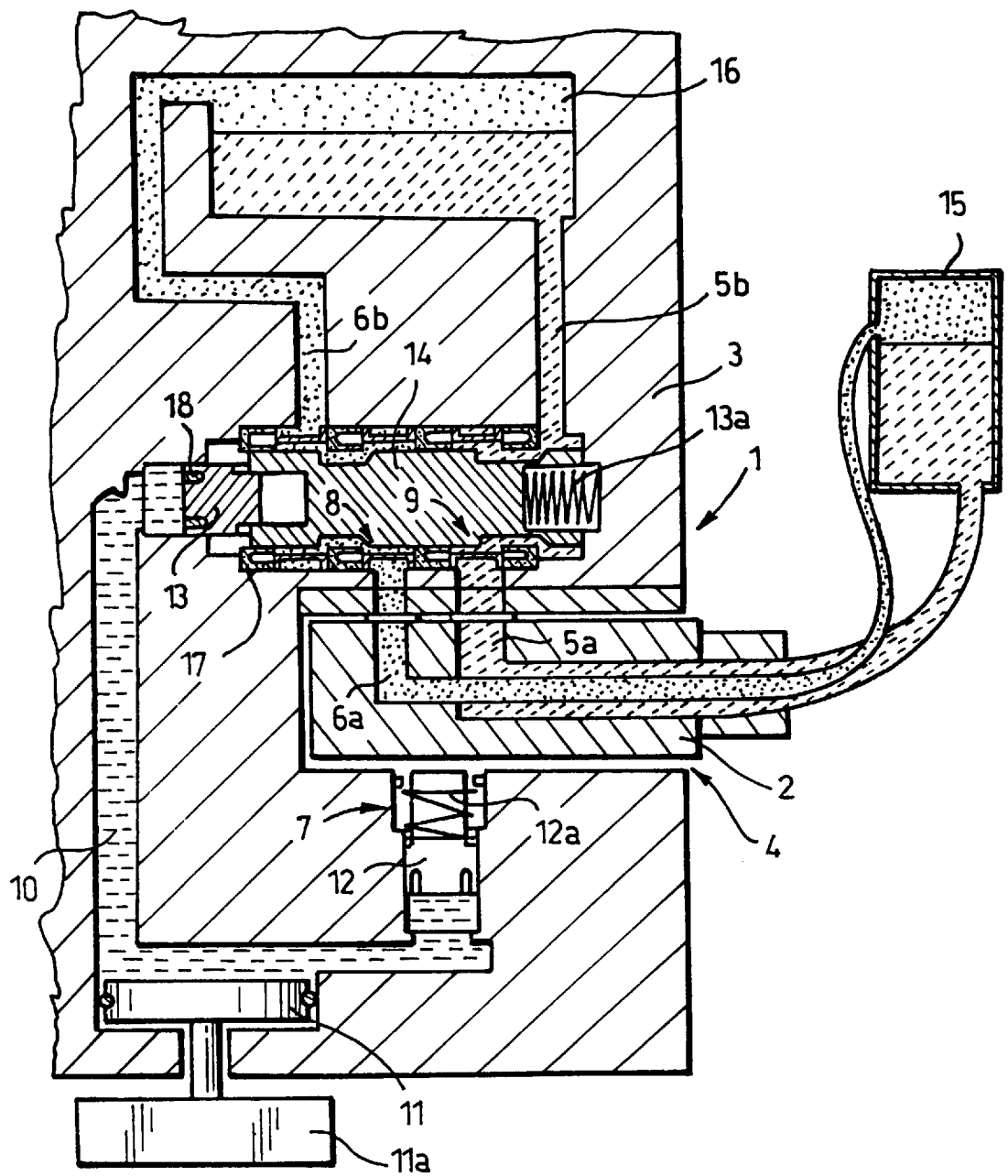
FIG. 1 illustrates in principle an assembly of the invention in the filling condition of an evaporator.
Figure 2:
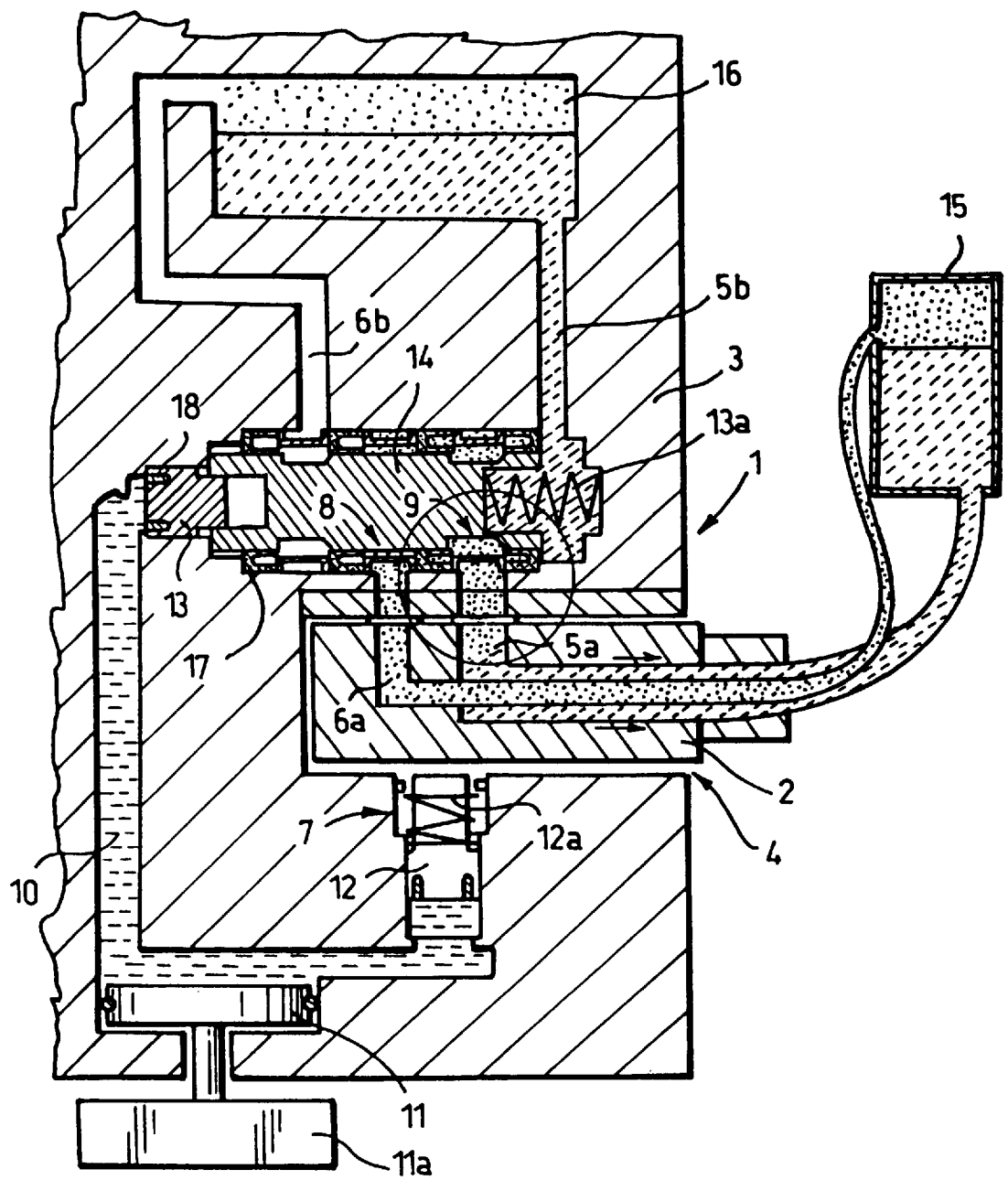
FIG. 2 shows the assembly of FIG. 1 in a condition, wherein the filling of an evaporator is completed

FIGS. 1–2 illustrate an assembly of the invention. Reference numeral 1 is used to generally designate a filling device. The filling device 1 includes a filling head 2, which can be inserted in an attachment point 4 included in an evaporator 3. The attachment point 4 can be provided e.g. in the form of a socket, which is the case in the illustrated embodiment. The filling device 1 and the evaporator 3 are provided with conduits 5a, 5b and 6a, 6b for carrying an anesthetic from a transport container into a liquid tank included in the evaporator and for delivering a substituting gas from the liquid tank of the evaporator into the transport container. For the sake of clarity, an anesthetic transport container 15 and an evaporator liquid tank 16 are only shown in principle in FIG. 1. For a person skilled in the art, these features represent totally conventional technology and, thus, such features are not described in further detail in this context.

The exemplary embodiment shown in the figures further comprises a clamping implement 7 for tightening the filling head against a wall of the socket serving as the attachment point 4 for the evaporator 3. Reference numerals 8 and 9 are used to generally designate valve elements, which are only adapted to open when the filling head 2 is in a position tightened against the wall of the evaporator attachment point 4 and hence to only allow a flow of anesthetic into the liquid tank of an evaporator and a flow of substituting gas into the anesthetic transport container when the filling head 2 is in a position tightened against the wall of the attachment point 4. The assembly according to the illustrated example comprises a hydraulic container 10, which is fitted with a first piston element 11 for the regulation of pressure existing within the hydraulic container 10, a second piston element 12 connected to the filling-head tightening implement 7, and a third piston element 13 connected to the valve elements 8, 9 which control the flow of anesthetic and substituting gas. Upon increasing the pressure in the hydraulic container 10, the second piston element 12 is adapted to tighten the filling head 2 against the wall of the evaporator attachment point 4 before the third piston element 13 commences, as a result of the increase of pressure in the hydraulic container, the process of opening the valve elements 8, 9 for allowing the flow of anesthetic and substituting gas and, respectively, upon decreasing the pressure in the hydraulic container 10, the third piston element 13 is adapted to close the valve elements 8, 9 before the second piston element 12 commences the process of loosening the tightening of the filling head 2 from a position compressed against the wall of the attachment point 4. It should be noted that the third piston element can also be adapted to apply only to the liquid-conduit valve element 9. Thus, the assembly can even be fitted with a fourth piston element, which applies to the gas-conduit valve element 8, or the gas-conduit valve element can be controlled by some other appropriate means. FIG. 1 depicts the condition, wherein the filling head 2 is tightened against a wall of the attachment point 4. On the other hand, FIG. 2 depicts the condition, wherein the filling of an evaporator is completed.

The second and third piston element 12, 13 can be preferably designed as spring-loaded elements in such a manner that a spring 12a included in the second piston element 12 is adapted to develop a lesser force than a spring 13a included in the third piston element 13. The above-described selection of springs can be used to accomplish in a preferred manner said tightening of the filling head and opening of the valve elements occurring in a proper sequence and, respectively, closing of the valve elements and release of the filling-head tightening. Operation of the assembly will be described in more detail as follows.

As pointed out above, the exemplary solution depicted in the figures is based on a liquid- or fluid-containing hydraulic container 10, which is fitted with three separate hydraulic pistons, piston elements 11, 12, 13. One piston 11 is linked to an actuator 11a, capable of operating the first piston element 11 and thus of regulating pressure existing in the container 10. In the illustrated example, the second piston element 12 is connected to a spring-returnable tightener for the filling head 2. The third piston element 13 is connected to a likewise spring-returnable filling valve 14, which is provided with the previously mentioned valve elements 8, 9. The tightening- or clamping-piston spring 12a is dimensioned to be lighter than the valve-piston spring 13a. As a result of this, upon using the actuator 11a to supply more pressure into the hydraulic system, the clamping piston 12 tightens the filling head 2 against the wall of the attachment point 4 prior to opening of the filling valve, i.e. valve elements 8, 9. However, the clamping piston does not necessarily require a spring at all provided that the pistons have kinetic frictions which are sufficiently low for returning the clamping piston by means of hydraulic suction. The opening of the filling valve 14, i.e. valve elements 8, 9, does not occur until the movement of the clamping piston stops as it comes into contact with the filling head 2 immobilized in the attachment point 4 of the evaporator. A result of the dimensioning is also an automatic closure of the filling valve 14 if the filling head 2 is disengaged while the valve elements 8, 9 are open and the clamping piston is able to freely advance deeper into the socket serving as the attachment point 4. Thirdly, the filling valve 14 does not open at all unless the filling head 2 is in its stationary position in the evaporator attachment point 4 when supplying pressure into the hydraulic system with the assistance of the actuator 11a, the clamping piston 12 pressing unimpededly into the socket serving as the filling-device attachment point 4.

In order to achieve the above-mentioned functions, the dimensioning of pistons and the displacements thereof must be effected by taking into consideration the volume changes of the hydraulic container 10 required for each piston. The volume change created by the filling-head 2 clamping piston, i.e. the second piston element 12, between the extreme points of a displacement is at least equal to the maximum change produced by the pressure regulation piston, i.e. the first piston element 11. The reason for this is that, if the filling head 2 is not immobilized in its position when the pressure regulation piston 11 is operated through the action of the actuator 11a, the entire volume change must be concentrated on the clamping piston 12 for maintaining the closed condition of the filling-valve piston, i.e. the third piston element 13, and respectively, the filling valve 14. On the other hand, the volume change produced by the filling-valve piston 13 must be lesser than that created by the pressure regulation piston 11, subtracted by that volume change of the clamping piston 12, which is maximally required for tightening the filling head 2 as it is immobilized in its position. The reason for this is that the available volume change is capable of both tightening the filling head 2 and still opening the filling valve 14. The volume change produced by the pressure regulation piston is determined from the foregoing.

In the commencing condition, the filling head 2 is fitted to the attachment point 4 included in an evaporator. When using the actuator 11a and the first piston element 11 for increasing pressure in the hydraulic container 10, the second piston element 12 begins to inch upwards in the situation shown in the figures and presses the filling head 2 against a wall of the attachment point 4, in other words, to the position shown in FIG. 1. After the filling head 2 has tightened itself in the position shown in FIG. 1 and as pressure is increased further, the third piston element 13 begins to inch to the right in the situation shown in the figures and carries at the same time the filling valve 14 to the right, whereby the valve elements 8, 9 open and allow the flow of an anesthetic liquid and a substituting gas, as described above, from a transport container 15 into an evaporator liquid tank 16 and, respectively, from the liquid tank 16 into the transport container 15.

When disengaging the filling head 2 from the attachment point, the pressure of the hydraulic container 10 is decreased, the third piston element 13 returning first to its initial position and at the same time closing the valve elements 8, 9 and, only thereafter, the second piston element returns to its initial position and releases the compression of the filling head 2 against a wall of the attachment point 4.

One preferred embodiment for liquid-flow and substituting-gas flow valves, i.e. the valve elements 8, 9, is to include the same in the elongated filling valve 14 sequentially along a common axis to extend, for example, in the direction of the filling-head attachment point 4 included in an evaporator in the immediate vicinity of flow conduits. Thus, the volume from the valve closing point to the filling head 2 is as small as possible. The invention relates essentially to an arrangement associated with the above-mentioned valves. Said arrangement will be described in more detail hereinbelow.

In terms of the opening sequence of the valve elements, it is essential that the gas-conduit valve element 8 not open prior to the liquid-conduit valve element 9. If this should happen, it might lead to the congestion of the gas conduit by the anesthetic liquid to preclude the filling. In case the liquid-conduit valve element 9 opens first, the liquid shall flow thereby towards the evaporator liquid tank 16 so as to induce, by means of a liquid column, an overpressure in the evaporator and an underpressure in the gas conduit. The pressure difference starts a powerful liquid flow as soon as the gas-conduit valve element 8 opens.

Between the gas conduits of the hydraulic fluid container 10 and the filling valve 14 are preferably fitted with both an actual piston packing 18 and also with a valve end packing 17. The double packing is provided in order to preclude the mixing of hydraulic fluid with anaesthetic liquid in case of damaged packing. A space between the packings 17, 18 can be preferably provided with a ventilation opening wherethrough, in case of a possible packing leak fluid, the leak shall escape out and mixing is avoided.

Figure 3:
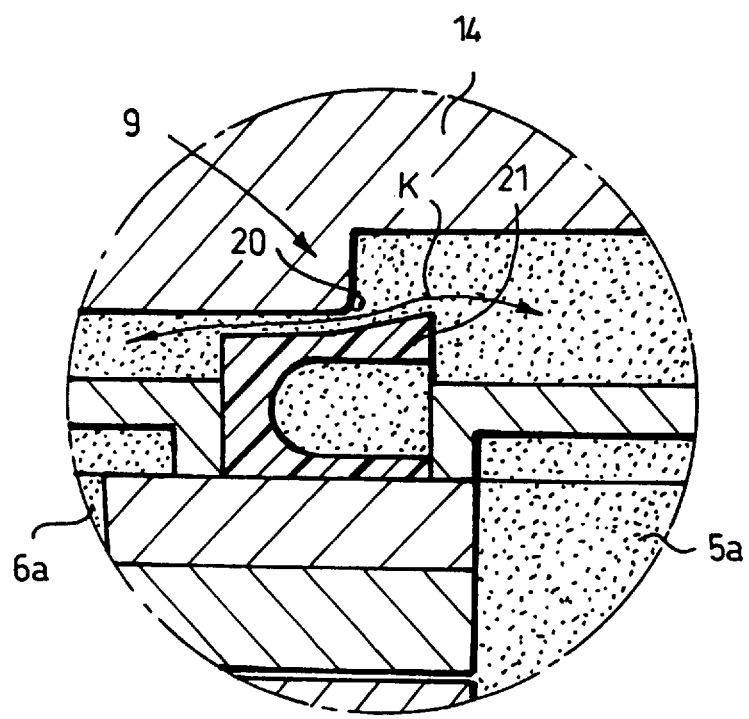
FIG. 3 shows one detail of a filling valve in the condition of FIG. 2.

According to the basic concept of the invention, the valve elements included in gas and liquid conduits are modified relative to the prior art solutions in such a manner that, as the conduits between the transport container 15 and the evaporator liquid tank 16 are closed, i.e. as the valve elements 8, 9 are shut off, the gas conduit 6a of a filling device closer to the transport container 15 and the corresponding liquid conduit 5a are connected to each other. In this context, the conduits 5a, 6a refer also to conduits included in the filling head 2. In the illustrated embodiment, the conduits 5a, 6a are adapted to be connected to each other in the filling valve 14. However, the conduits 5a, 6a can also be connected to each other not just in the filling valve, an example of this being a connection effected in the filling head in the vicinity of the valve elements 8, 9. In practice the connection of the conduits 5a, 6a is preferably effected as near the valve elements 8, 9 as possible, since the evacuation shall then occur as quickly and completely as possible. FIG. 2 depicts a situation, wherein the filling of the liquid tank 16 is completed but the filling head has not yet been released from compression. In this situation, the conduits between transport container 15 and the evaporator liquid tank 16 are closed and the gas conduit 6a and the liquid conduit 5a are in communication with each other in the filling valve 14, as pointed out above. FIG. 3 illustrates in an enlarged scale as to how the gas and liquid conduits are connected to each other inside the filling head in the example shown in FIGS. 1 and 2. FIG. 3 includes an arrow K to indicate a conduit connecting the gas and liquid conduit. FIG. 2 includes a circle to indicate a detail depicted in FIG. 3. In the illustrated embodiment, as the conduits 5a, 6a between the transport container and the liquid tank are closed, i.e. as the valve elements 8, 9 are shut off but the filling head continues to be clamped in the attachment point, a cut-off element 20 is adapted to open between the conduits for allowing the liquid to flow back into the transport container. The cut-off element 20 is in an open position in FIG. 3. The communication between the conduits 5a, 6a is closed whenever the cut-off element 20 squeezes against a packing 21 shown in FIG. 3.

In an assembly of the invention, the filling valves develop no vacuum since, as the liquid flows along one conduit towards the transport container, a substituting gas is allowed to flow from the transport container towards the filling valve. FIG. 2 includes arrows to indicate the flow of liquid and substituting gas in this situation. Thus, the entire filling device drains itself quickly of the anesthetic liquid back into the transport container whereby, upon removing the filling device from the evaporator, the liquid retained between the filling device sealing and the filling valve cannot leak into the environment.

However, the above-described exemplary embodiment is by no means intended to limit the invention but, instead, the invention can be modified with no restrictions within the scope of the appended claims. Thus, it is obvious that an assembly of the invention or details thereof need not be exacly as depicted in the figures, but other types of solutions are conceivable as well. In the illustrated example, the invention is discussed in association with a certain type of solution. However, the invention is by no means limited to such an embodiment but, instead, the invention can be applied to any apparatus in which an evaporator is filled by connecting therewith a container carrying an anesthetic liquid.

We claim:

1. A method for filling a liquid tank of an anaesthetic evaporator from an anaesthetic transport container by means of a filling device connectable to the anaesthetic transport container and having a filling head, the filling head having a conduit for passing liquid anaesthetic in a given direction between the transport container and the evaporator and a conduit for passing a substituting gas in the opposite direction between the transport container and the evaporator, the conduits having openings on a surface of the filling head, said method comprising the steps of:

inserting the filling head in an attachment socket in the evaporator, the evaporator having conduits corresponding to the conduits of the filling head and opening into said attachment socket along a sealing surface;

compressively applying the surface of the filling head to the sealing surface of the attachment socket to place the conduit openings of the filling head and attachment socket in registration;

operating a valve means in the evaporator connected between the conduits in the evaporator and liquid and gas passages leading from said valve means to the liquid tank, the valve means being operated between an open condition that allows anaesthetic to flow between the evaporator and the transport container in a given direction and substituting gas to flow in the opposite direction between the evaporator and the transport container and a closed condition which blocks the flow of anaesthetic and gas; and connecting an anaesthetic conduit and a substituting gas conduit together to form a confined connecting path when the passage of anesthesia and gas is blocked by said valve means for facilitating return of the liquid anaesthetic to the transport container and draining of the liquid anaesthetic from said conduits.

2. A method as set forth in claim 1 further defined as connecting an anaesthetic conduit and a substituting gas conduit together in the valve means.

3. A method as set forth in claim 2 further defined as connecting an anaesthetic conduit and a substituting gas conduit together when the valve means is in the closed condition.

4. A method as set forth in claim 2 further defined as connecting an anaesthetic conduit and a substituting gas conduit together when the valve means is the closed condition and prior to releasing compression on the filling head.

5. A method as set forth in claim 4 wherein operation of the valve means and compressive application of the surface of the filling head to the sealing surface of the attachment socket are carried out by a common, pressurizable hydraulic circuit and wherein releasing pressure on the hydraulic circuit initiates operation of the valve means prior to releasing compression on the filling head.

6. A method as set forth in claim 1 further defined as connecting an anaesthetic conduit and a substituting gas conduit together when the valve means is in the closed condition.

7. A method as set forth in claim 1 further defined as operating the valve means such that the valve means assumes the open condition after insertion of the filling head in the attachment socket and compressive application of the surface of the filling head to the sealing surface of the attachment socket.

8. A method as set forth in claim 1 further defined as operating the valve to commence the flow of anaesthetic before the flow of substituting gas when the valve assumes the open condition.

9. A method as set forth in claim 1 further defined as positioning the valve means approximate to the sealing surface of the attachment socket for rendering the length of the conduits in the evaporator short.

10. An assembly for filling a liquid tank of an anaesthetic evaporator from an anaesthetic transport container by means of a filling device connectable to the anaesthetic transport container and having a filling head, said filling head having a conduit for passing liquid anaesthetic in a given direction between the transport container and the evaporator and a conduit for passing a substituting gas in the opposite direction between the transport container and the evaporator, the conduits having openings on a surface of the filling head, said assembly comprising:

an attachment socket in the evaporator for receiving the filling head, the evaporator having conduits corresponding to the conduits of the filling head and opening into said attachment socket along a sealing surface;

clamping means operable to compressively apply the surface of the filling head to said sealing surface of said attachment socket with the conduit openings of the filling head and attachment socket in registration;

valve means in the evaporator, said valve means being connected between said conduits in the evaporator and liquid and gas passages leading from said valve means to the liquid tank, said valve having an open condition to allow anaesthetic to flow between the evaporator and the transport container in a given direction and substituting gas to flow in the opposite direction between the evaporator and the transport container, said valve means having a closed condition which blocks the flow of anaesthetic and gas; and connection means providing a confined path connecting an anesthesia conduit and a substituting gas conduit together when the flow of anesthesia and gas is blocked by said valve means for facilitating return of the liquid anaesthetic to the transport container and draining of the liquid anaesthetic from said conduits.

11. An assembly as set forth in claim 10 wherein said connection means provides said connecting path in said valve means.

12. An assembly as set forth in claim 11 wherein said valve means is formed to provide said connecting path when said valve means is in the closed condition.

13. An assembly as set forth in claim 11 wherein said valve means has an operator and wherein the operator of said valve means and said clamping means are operated such that said connecting path is formed in said valve means prior to said clamping means releasing compression on the filling head.

14. An assembly as set forth in claim 13 wherein said valve means and said clamping means are operated by a common, pressurizable hydraulic circuit and wherein releasing pressure on said hydraulic circuit initiates operation of said valve means before said clamping means.

15. An assembly as set forth in claim 14 wherein said operator for said valve means and said clamping means have biasing springs and wherein said biasing spring in said valve means exerts a lesser force than said biasing spring in said clamping means for initiating operation of said valve means before said clamping means when the pressure on said hydraulic circuit is released.

16. An assembly as set forth in claim 10 wherein said valve means is proximate to said sealing surface of said attachment socket for rendering the length of said conduits in said evaporator short.

17. An assembly as set forth in claim 10 wherein said valve means and said clamping means are operated such that said valve means assumes the open condition after the filling head has been received in said attachment socket and compressively applied to said sealing surface of said attachment socket.

18. As assembly as set forth in claim 10 wherein said valve means is formed to commence flow of anaesthetic before the flow of substituting gas when the valve assumes the open condition.

* * * * *